United States Patent
Stahmann et al.

(10) Patent No.: US 6,922,589 B2
(45) Date of Patent: *Jul. 26, 2005

(54) SITE REVERSION IN CARDIAC RHYTHM MANAGEMENT

(75) Inventors: Jeffrey E. Stahmann, Ramsey, MN (US); Andrew P. Kramer, Stillwater, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/314,875

(22) Filed: Dec. 9, 2002

(65) Prior Publication Data

US 2003/0176894 A1 Sep. 18, 2003

Related U.S. Application Data

(63) Continuation of application No. 09/650,568, filed on Aug. 30, 2000, now Pat. No. 6,493,586.

(51) Int. Cl.$^7$ .............................................. A61N 1/368
(52) U.S. Cl. .......................................... 607/27; 607/28
(58) Field of Search ................................ 600/372–374, 600/377, 381, 54, 547; 607/4–5, 8–9, 27–28, 115–116, 119, 121–123

(56) References Cited

U.S. PATENT DOCUMENTS

| | | | |
|---|---|---|---|
| 3,835,864 A | 9/1974 | Rasor et al. | 128/419 P |
| 3,943,936 A | 3/1976 | Rasor et al. | 128/419 P |
| 4,091,817 A | 5/1978 | Thaler | 128/419 PG |
| 4,122,294 A | 10/1978 | Frolov | 13/18 R |
| RE30,366 E | 8/1980 | Rasor et al. | 128/419 P |
| 4,332,259 A | 6/1982 | McCorkle, Jr. | 128/786 |
| 4,399,818 A | 8/1983 | Money | 128/419 PG |
| 4,401,119 A | 8/1983 | Herpers | 128/419 PG |
| 4,402,330 A | 9/1983 | Lindemans | 128/786 |
| 4,407,287 A | 10/1983 | Herpers | 28/419 PG |

(Continued)

FOREIGN PATENT DOCUMENTS

| | | | |
|---|---|---|---|
| EP | 0488512 | 10/1990 | |
| EP | 1013303 | 6/2000 | A61N/1/05 |
| JP | 5-049701 | 3/1993 | A61N/1/05 |

OTHER PUBLICATIONS

Stahmann, Jeffrey E., et al., "Safety Pacing in Multi–Site CRM Devices", *U.S. Appl. No. 10/839,268, filed May 5, 2004*, 42 pgs.

*Primary Examiner*—Kennedy Schaetzle
*Assistant Examiner*—Kristen Mullen
(74) *Attorney, Agent, or Firm*—Schwegman, Lundberg, Woessner & Kluth, P.A.

(57) ABSTRACT

Methods for failure recovery in a cardiac rhythm management system and apparatus capable of carrying out the methods. The methods include applying a first pacing therapy using one or more leads. The methods further include detecting a failure condition on one or more of the leads, wherein the failure condition prohibits or frustrates application of the first pacing therapy. The methods still further include applying a second pacing therapy using one or more of the leads subsequent to detecting the failure condition. The second pacing therapy is preferably chosen such that the detected failure does not interfere with the second pacing therapy. The second pacing therapy may be applied for only one cardiac cycle. The second pacing therapy may further be applied continuously until the failure condition is resolved, or it may be latched such that physician intervention is required to resume the first pacing therapy.

33 Claims, 7 Drawing Sheets

U.S. PATENT DOCUMENTS

| | | | | |
|---|---|---|---|---|
| 4,408,608 A | 10/1983 | Daly et al. | | 128/421 |
| 4,458,677 A | 7/1984 | McCorkle, Jr. | | 128/786 |
| 4,577,639 A | 3/1986 | Simon et al. | | 128/709 |
| 4,592,359 A | 6/1986 | Galbraith | | 128/419 R |
| 4,665,925 A | 5/1987 | Millar | | 128/663 |
| 4,889,128 A | 12/1989 | Millar | | 128/662.06 |
| 4,928,688 A | 5/1990 | Mower | | 128/419 PG |
| 4,932,407 A | 6/1990 | Williams | | 128/419 D |
| 4,957,111 A | 9/1990 | Millar | | 128/662.06 |
| 4,958,632 A | * 9/1990 | Duggan | | 607/11 |
| 5,014,696 A | 5/1991 | Mehra | | 128/419 D |
| 5,076,272 A | 12/1991 | Ferek-Petric | | 128/419 |
| 5,099,838 A | 3/1992 | Bardy | | 128/419 D |
| 5,144,960 A | 9/1992 | Mehra et al. | | 128/786 |
| 5,165,403 A | 11/1992 | Mehra | | 128/419 D |
| 5,167,229 A | 12/1992 | Peckham et al. | | 128/421 |
| 5,226,427 A | 7/1993 | Buckberg et al. | | 128/772 |
| 5,277,231 A | 1/1994 | Dostalek | | 140/106 |
| 5,308,356 A | 5/1994 | Blackshear, Jr. et al. | | 606/194 |
| 5,318,593 A | 6/1994 | Duggan | | 607/9 |
| 5,331,966 A | 7/1994 | Bennett et al. | | 128/696 |
| 5,372,125 A | 12/1994 | Lyons | | 128/64 D |
| 5,387,233 A | 2/1995 | Alferness et al. | | 607/126 |
| 5,405,374 A | 4/1995 | Stein | | 607/122 |
| 5,409,469 A | 4/1995 | Schaerf | | 604/282 |
| 5,411,524 A | 5/1995 | Rahul | | 607/4 |
| 5,423,806 A | 6/1995 | Dale et al. | | 606/15 |
| 5,441,504 A | 8/1995 | Pohndorf et al. | | 606/129 |
| 5,465,715 A | 11/1995 | Lyons | | 128/640 |
| 5,476,498 A | 12/1995 | Ayers | | 607/122 |
| 5,540,727 A | 7/1996 | Tockman et al. | | 607/18 |
| 5,549,642 A | 8/1996 | Min et al. | | 607/5 |
| 5,578,069 A | 11/1996 | Miner, II | | 607/126 |
| 5,609,621 A | 3/1997 | Bonner | | 607/122 |
| 5,639,276 A | 6/1997 | Weinstock et al. | | 606/129 |
| 5,674,217 A | 10/1997 | Wahlstrom et al. | | 606/15 |
| 5,674,255 A | 10/1997 | Walmsley et al. | | 607/14 |
| 5,683,445 A | 11/1997 | Swoyer | | 607/125 |
| 5,700,283 A | 12/1997 | Salo | | 607/17 |
| 5,704,351 A | 1/1998 | Mortara et al. | | 128/630 |
| 5,713,867 A | 2/1998 | Morris | | 604/164 |
| 5,720,768 A | 2/1998 | Verboven-Nelissen | | 607/9 |
| 5,744,038 A | 4/1998 | Cham | | 210/634 |
| 5,755,761 A | 5/1998 | Obino | | 607/122 |
| 5,755,766 A | 5/1998 | Chastain et al. | | 607/122 |
| 5,769,875 A | 6/1998 | Peckham et al. | | 607/48 |
| 5,772,693 A | 6/1998 | Brownlee | | 607/123 |
| 5,776,073 A | 7/1998 | Garfield et al. | | 600/546 |
| 5,776,171 A | 7/1998 | Peckham et al. | | 607/48 |
| 5,782,879 A | 7/1998 | Rosborough et al. | | 607/6 |
| 5,800,495 A | 9/1998 | Machek et al. | | 607/116 |
| 5,803,928 A | 9/1998 | Tockman et al. | | 607/122 |
| 5,814,088 A | 9/1998 | Paul et al. | | 607/28 |
| 5,824,032 A | 10/1998 | Belden | | 607/126 |
| 5,843,117 A | 12/1998 | Alt et al. | | 606/194 |
| 5,871,529 A | 2/1999 | Bartig et al. | | 607/122 |
| 5,871,531 A | 2/1999 | Struble | | 607/126 |
| 5,897,577 A | * 4/1999 | Cinbis et al. | | 607/28 |
| 5,902,324 A | 5/1999 | Thompson et al. | | 607/9 |
| 5,913,887 A | 6/1999 | Michel | | 607/123 |
| 5,922,014 A | 7/1999 | Warman et al. | | 607/123 |
| 5,925,073 A | 7/1999 | Chastain et al. | | 607/122 |
| 5,931,864 A | 8/1999 | Chastain et al. | | 607/128 |
| 5,935,160 A | 8/1999 | Auricchio et al. | | 607/122 |
| 5,954,758 A | 9/1999 | Peckham et al. | | 607/48 |
| 5,978,707 A | 11/1999 | Krig et al. | | 607/14 |
| 5,983,138 A | 11/1999 | Kramer | | 607/9 |
| 6,006,137 A | 12/1999 | Williams | | 607/119 |
| 6,014,581 A | 1/2000 | Whayne et al. | | 600/523 |
| 6,026,328 A | 2/2000 | Peckham et al. | | 607/48 |
| 6,027,462 A | 2/2000 | Greene et al. | | 600/585 |
| 6,049,732 A | 4/2000 | Panescu et al. | | 600/523 |
| 6,055,457 A | 4/2000 | Bonner | | 607/126 |
| 6,061,594 A | 5/2000 | Zhu et al. | | 607/28 |
| 6,070,104 A | 5/2000 | Hine et al. | | 607/123 |
| RE36,765 E | 7/2000 | Mehra | | 607/4 |
| 6,106,460 A | 8/2000 | Panescu et al. | | 600/300 |
| 6,112,117 A | 8/2000 | KenKnight et al. | | 607/5 |
| 6,115,626 A | 9/2000 | Whayne et al. | | 600/427 |
| 6,129,750 A | 10/2000 | Tockman et al. | | 607/125 |
| 6,132,456 A | 10/2000 | Sommer et al. | | 607/127 |
| 6,144,880 A | 11/2000 | Ding et al. | | 607/23 |
| 6,148,233 A | 11/2000 | Owen et al. | | 607/5 |
| 6,159,237 A | 12/2000 | Alt et al. | | 623/1.11 |
| 6,163,725 A | 12/2000 | Peckham et al. | | 607/61 |
| 6,256,536 B1 | 7/2001 | Kramer | | 607/9 |
| 6,285,907 B1 | 9/2001 | Kramer et al. | | 607/9 |
| 6,292,693 B1 | 9/2001 | Darvish et al. | | 607/9 |
| 6,363,288 B1 | 3/2002 | Bush et al. | | 607/122 |
| 6,370,430 B1 | 4/2002 | Mika et al. | | 607/9 |
| 6,385,492 B1 | 5/2002 | Ollivier et al. | | 607/122 |
| 6,480,740 B2 | 11/2002 | Stahmann et al. | | 607/9 |
| 6,493,586 B1 | * 12/2002 | Stahmann et al. | | 607/27 |
| 6,584,362 B1 | 6/2003 | Scheiner et al. | | |
| 6,615,089 B1 | * 9/2003 | Russie et al. | | 700/21 |
| 6,662,055 B1 | 12/2003 | Prutchi | | 607/122 |
| 2001/0016759 A1 | 8/2001 | Kramer et al. | | 607/9 |
| 2001/0031993 A1 | 10/2001 | Salo et al. | | 607/9 |
| 2001/0041918 A1 | 11/2001 | Baker et al. | | 607/9 |
| 2002/0055764 A1 | 5/2002 | Malonek et al. | | 607/122 |
| 2003/0069607 A1 | 4/2003 | Stahmann et al. | | 607/9 |
| 2003/0195603 A1 | 10/2003 | Scheiner et al. | | 607/122 |

\* cited by examiner

SITE REVERSION IN CARDIAC RHYTHM MANAGEMENT

CROSS-REFERENCE TO RELATED APPLICATIONS

This application is a continuation of U.S. patent application Ser. No. 09/650,568, filed on Aug. 30, 2000, now U.S. Pat. No. 6,493,586 the specification of which is hereby incorporated by reference.

This application is related to co-pending, commonly assigned U.S. patent application Ser. No. 09/651,340, filed on Aug. 30, 2000, the specification of which is hereby incorporated by reference.

TECHNICAL FIELD

The invention relates generally to cardiac rhythm management systems, and particularly, but not by way of limitation, to a system providing, among other things, reversionary behavior in multi-chamber pacing therapy.

BACKGROUND

When functioning properly, the human heart maintains its own intrinsic rhythm, and is capable of pumping adequate blood throughout the body's circulatory system. However, some people have irregular cardiac rhythms, referred to as cardiac arrhythmias. Such arrhythmias result in diminished blood circulation. One mode of treating cardiac arrhythmias includes the use of a cardiac rhythm management system. Such systems are often implanted in the patient and deliver therapy to the heart.

Cardiac rhythm management systems include, among other things, pacemakers, also referred to as pacers. Pacers deliver timed sequences of low energy electrical stimuli, called pace pulses, to the heart, such as via an intravascular lead (referred to as a "lead") having one or more electrodes disposed in or about the heart. Heart contractions are initiated in response to such pace pulses (this is referred to as "capturing" the heart). By properly timing the delivery of pace pulses, the heart can be induced to contract in proper rhythm, greatly improving its efficiency as a pump. Pacers are often used to treat patients with bradyarrhythmias, that is, hearts that beat too slowly, or irregularly.

Cardiac rhythm management systems also include cardioverters or defibrillators that are capable of delivering higher energy electrical stimuli to the heart. Defibrillators are often used to treat patients with tachyarrhythmias, that is, hearts that beat too quickly. Such too-fast heart rhythms also cause diminished blood circulation because the heart isn't allowed sufficient time to fill with blood before contracting to expel the blood. Such pumping by the heart is inefficient. A defibrillator is capable of delivering a high energy electrical stimulus that is sometimes referred to as a defibrillation countershock. The countershock interrupts the tachyarrhythmia, allowing the heart to reestablish a normal rhythm for the efficient pumping of blood. In addition to pacers, cardiac rhythm management systems also include, among other things, pacer/defibrillators that combine the functions of pacers and defibrillators, drug delivery devices, and any other implantable or external systems or devices for diagnosing or treating cardiac arrhythmias.

One problem faced by cardiac rhythm management systems is the treatment of congestive heart failure (also referred to as "CHF"). In some forms, congestive heart failure can be treated by biventricular coordination therapy that provides pacing pulses to both right and left ventricles, by biatrial coordination therapy that provides pacing pulses to both the right and left atrium, or other multichamber coordination therapy. Biventricular and biatrial coordination therapy each rely on multiple leads and multielectrode leads to carry out the coordination therapy of multiple chambers of the heart. In the event of a failure in one or more of these leads, or their associated circuity, the ability to perform coordination therapy is generally lost.

As will be seen from the above concerns, there exists a need for improved failure recovery mechanisms in cardiac rhythm management systems used in biventricular and/or biatrial coordination therapy. The above-mentioned problems with failure recovery and other problems are addressed by the various embodiments of the invention and will be understood by reading and studying the following specification.

SUMMARY

The various embodiments of the invention include methods for failure recovery in a cardiac rhythm management system and apparatus capable of carrying out the methods. The methods include applying a first pacing therapy using one or more leads and/or electrodes. The methods further include detecting a failure condition on one or more of the leads and/or electrodes, wherein the failure condition prohibits or frustrates application of the first pacing therapy. The methods still further include subsequently applying a second pacing therapy using a new combination of one or more of the leads and/or electrodes. The second pacing therapy is preferably chosen such that the detected failure does not interfere with the second pacing therapy. The second pacing therapy may be applied for only one cardiac cycle. The second pacing therapy may further be applied continuously until the failure condition is resolved, or it may be latched such that physician intervention is required to resume the first pacing therapy.

One embodiment includes a method of delivering pacing therapy to a heart. The method includes delivering a first therapy to a first and second electrode coupled to the heart, detecting a failure associated with the first electrode, discontinuing the first therapy during a period of the failure associated with the first electrode, and delivering a second therapy to the second electrode during the period of the failure associated with the first electrode.

Another embodiment includes a method of delivering pacing therapy to a heart. The method includes delivering a first therapy to a first and second electrode of a lead adapted for implantation on or about the heart. The lead includes a main lead body adapted to carry signals to and from the heart, a first electrode associated with the main lead body, and a second electrode associated with the main lead body. The first and second electrodes are routed through the coronary sinus upon implantation. The method further includes detecting a failure associated with the first electrode, discontinuing the first therapy during a period of the failure associated with the first electrode, and delivering a second therapy to the second electrode during the period of the failure associated with the first electrode.

A further embodiment includes a cardiac rhythm management system. The system includes a first electrode adapted to couple to a first chamber of a heart, a second electrode adapted to couple to a second chamber of the heart, a signal generator for producing pulses to apply to the heart, wherein the signal generator is coupled to the first electrode and the second electrode for applying the pulses, and a processor coupled to the signal generator. The processor is adapted to cause the signal generator to deliver a first therapy to the first electrode in the absence of a failure detection associated with the first electrode, and to deliver a second therapy to the second electrode in the presence of a failure detection associated with the first electrode.

A still further embodiment includes a cardiac rhythm management system. The system includes a signal generator for producing pulses to apply to the heart and a lead adapted for implantation on or about the heart and for connection to the signal generator, wherein the lead includes a main lead body adapted to carry signals to and from the heart, a first electrode associated with the main lead body and a second electrode associated with the main lead body, the first and second electrodes being routed through the coronary sinus upon implantation. The system further includes a processor coupled to the signal generator, wherein the processor is adapted to cause the signal generator to deliver a first therapy to at least the first electrode in the absence of a failure associated with the first electrode, and to deliver a second therapy to the second electrode in the presence of a failure associated with the first electrode.

An additional embodiment of the cardiac rhythm management system includes both a first and a second lead, where both leads have at least one electrode to sense cardiac signals and to deliver pulses to the heart. The system further includes a processor coupled to a signal generator, were the signal generator produces pulses to apply through the electrode(s) on the first and second leads. The processor is adapted to cause the signal generator to deliver a first therapy through the at least one electrode of the first lead and to deliver a second therapy through the at least one electrode of the second lead in the presence of a failure detection associated with the first lead.

Other embodiments include methods and apparatus of varying scope.

DESCRIPTION OF THE EMBODIMENTS

Figure 1:
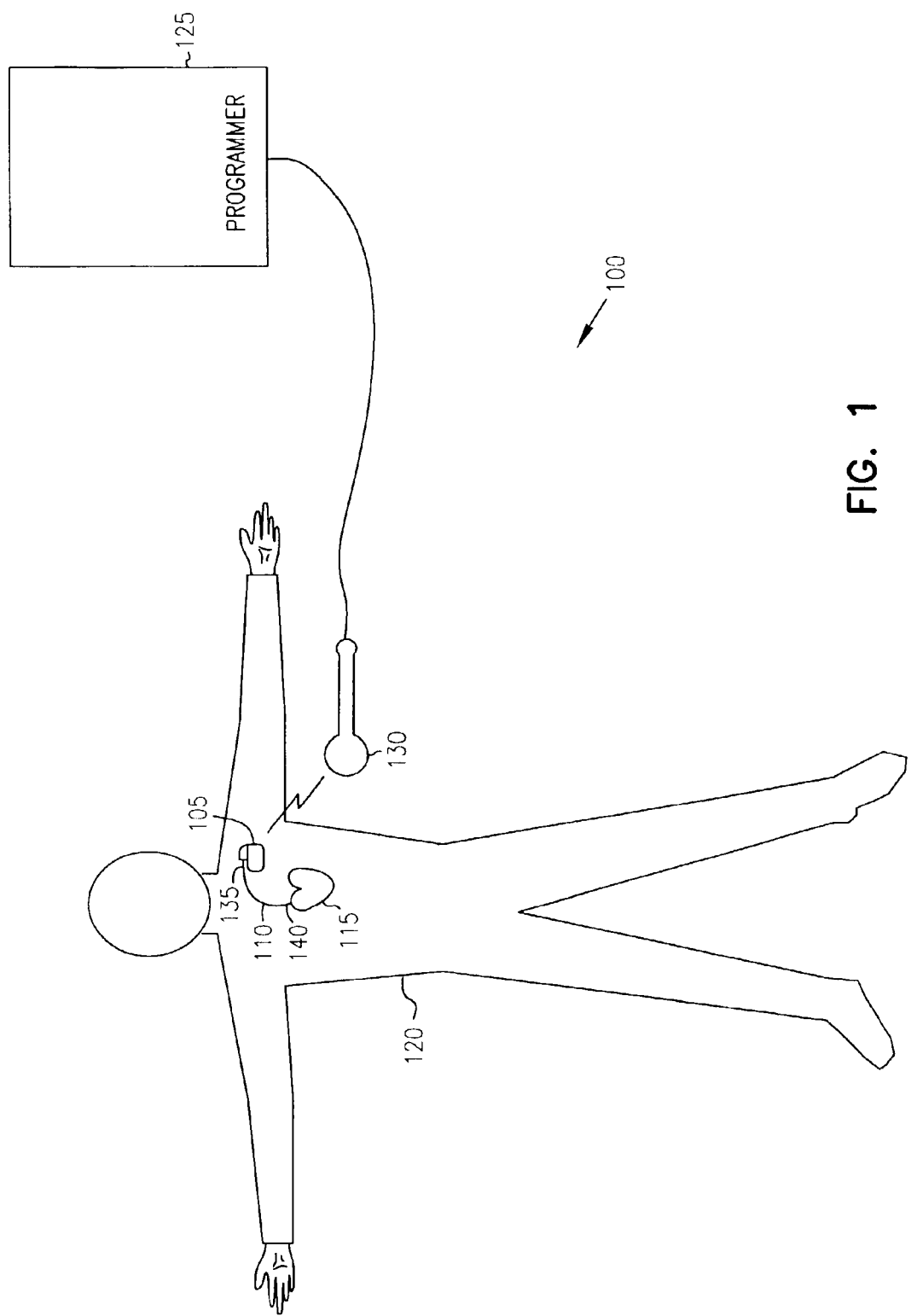
FIG. 1 is a schematic drawing illustrating generally one embodiment of portions of a cardiac rhythm management system and an environment in which it is used.

In the following detailed description, reference is made to the accompanying drawings which form a part hereof, and in which is shown by way of illustration specific embodiments in which the invention may be practiced. These embodiments are described in sufficient detail to enable those skilled in the art to practice the invention, and it is to be understood that other embodiments may be utilized and that structural, logical and electrical changes may be made without departing from the spirit and scope of the invention. The following detailed description is, therefore, not to be taken in a limiting sense, and the scope of the invention is defined by the appended claims and their equivalents. Like numbers in the figures refer to like components, which should be apparent from the context of use.

The various embodiments will generally be discussed in the context of biventricular pacing therapies, having leads coupled to both the right and left ventricles. However, it should be apparent that the methods described herein can be readily adapted to biatrial pacing therapies, having leads coupled to both the right and left atrium, as well as other multichamber pacing therapies, e.g., one atrium/two ventricles, two atriums/two ventricles, etc. Furthermore, the methods described herein can be readily adapted to unichamber therapies, having multiple lead sites within a single chamber.

The presence of multiple lead sites permits useful reversionary behavior. Specifically, it permits therapy reversion to an alternate lead, electrode and/or site if an anomaly or failure is detected in the programmed lead, electrode and/or site. For example, if an anomaly is detected in the right ventricle (RV) lead, electrode and/or site during biventricular pacing, reversion to a lead, electrode and/or site in the left ventricle (LV) would permit initiation of univentricular LV pacing. While the coordinating therapy may be lost during the period of reversion, the patient would still receive potentially life-sustaining rate therapy. As a further example, if an anomaly is detected in the LV lead, electrode and/or site during univentricular LV pacing, reversion to a lead, electrode and/or site in the RV would permit initiation of univentricular RV pacing. In this example, the multiple leads and/or electrodes operate as a redundant system.

The cardiac rhythm management systems of the various embodiments may generally be used with conventional pacing modes, such as DDD, VVI, AAI, etc. Pacing modes are generally represented by three or four letters. The first three letters of the pacing mode generally represent Pace, Sense, and Operating Algorithm. The first two letters are expressed as A (Atrial), V (Ventricle) or D (Dual, both atrial and ventricular). The third letter generally represents T (triggered), I (inhibited), or D (for both T and I). A fourth letter in the description, such as R which indicates Rate response, is used to describe an additional feature of the pacemaker. These pacing modes are generally well known in the art, and will not be discussed in detail herein.

FIG. 1 is a schematic drawing illustrating, by way of example, but not by way of limitation, one embodiment of portions of a cardiac rhythm management system 100 and an environment in which it is used. In FIG. 1, system 100 includes an implantable pacemaker 105, also referred to as an electronics unit, which is coupled by an intravascular endocardial lead 110, or other lead, to a heart 115 of patient 120. Pacemaker 105 is adapted to perform the methods as described herein. System 100 also includes an external programmer 125 providing wireless communication with pacemaker 105 using a telemetry device 130, such as might be used by a physician to initially program or periodically reprogram pacemaker 105. Endocardial lead 110 includes a proximal end 135, which is coupled to pacemaker 105, and a distal end 140, which is coupled to one or more portions of heart 115.

Figure 2:
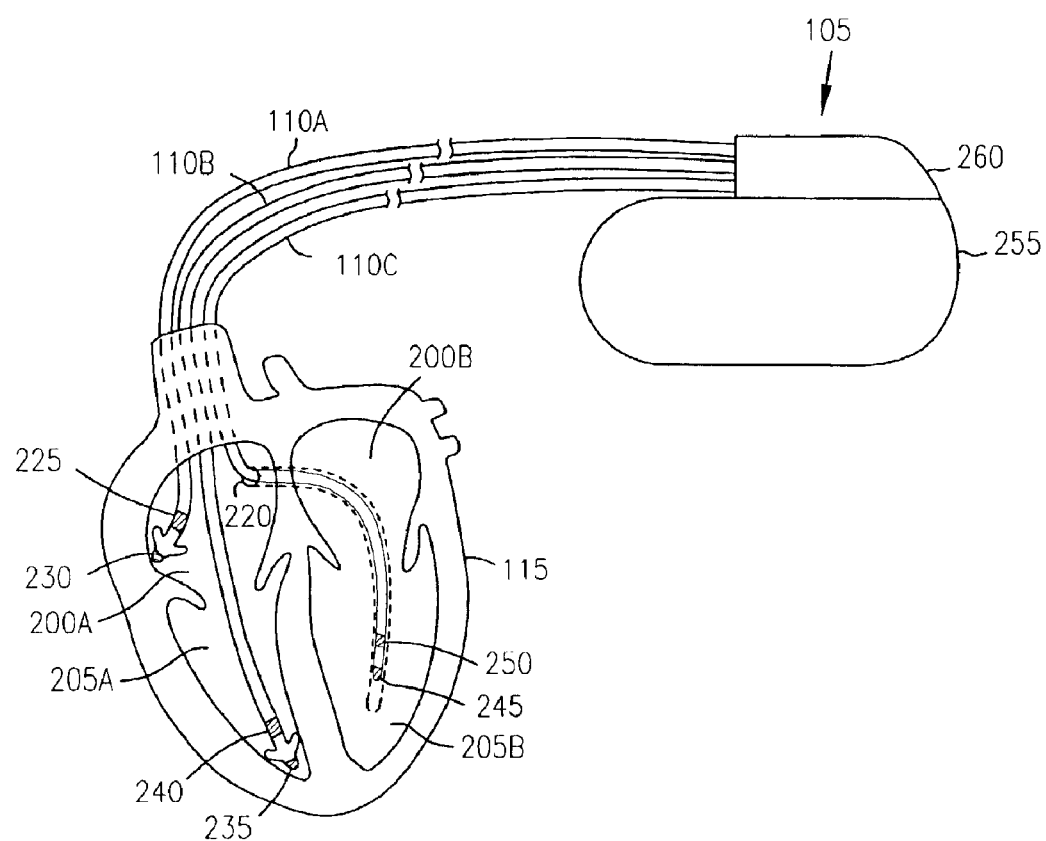
FIG. 2 is a schematic drawing illustrating one embodiment of a cardiac rhythm management device coupled by leads to a heart.

FIG. 2 is a schematic drawing illustrating, by way of example, but not by way of limitation, one embodiment of device 105 coupled by leads 110A–C to a heart 115, which includes a right atrium 200A, a left atrium 200B, a right ventricle 205A, a left ventricle 205B, and a coronary sinus 220 extending from right atrium 200A. In one such embodiment, system 100 provides biventricular coordination therapy to coordinate right ventricular and left ventricular contractions, such as for congestive heart failure patients. In this embodiment, atrial lead 110A includes electrodes (electrical contacts) disposed in, around, or near the right atrium 200A of heart 115, such as ring electrode 225 and tip electrode 230, for sensing signals and/or delivering pacing therapy to the right atrium 200A. Lead 110A optionally also includes additional electrodes, such as for delivering atrial and/or ventricular cardioversion/defibrillation and/or pacing therapy to heart 115. The embodiment further includes a right ventricular lead 110B having one or more electrodes disposed in, around, or near the right ventricle 205A, such as tip electrode 235 and ring electrode 240, for delivering sensing signals and/or delivering pacing therapy. Lead 110B optionally also includes additional electrodes, such as for delivering atrial and/or ventricular cardioversion/ defibrillation and/or pacing therapy to heart 115. The embodiment further includes a left ventricular lead 110C, inserted through coronary sinus 220 and into the great cardiac vein so that its electrodes, which include electrodes 245 and may optionally include electrode 250, are associated with left ventricle 205B for sensing intrinsic heart signals and providing one or more of coordination paces or defibrillation shocks. Lead 110C optionally also includes additional electrodes, such as for delivering atrial and/or ventricular cardioversion/defibrillation and/or pacing therapy to heart 115.

In FIG. 2, device 105 includes components that are enclosed in a hermetically-sealed can 255. Additional electrodes may be located on the can 255, may be the can 255 itself, may be on an insulating header 260, or on other portions of device 105, for providing unipolar or bipolar pacing/sensing and/or defibrillation energy in conjunction with the electrodes disposed on or around heart 115. Other forms of electrodes include meshes and patches which may be applied to portions of heart 115 or which may be implanted in other areas of the body to help "steer" electrical currents produced by device 105. The present method and apparatus will work in a variety of configurations and with a variety of electrical contacts or "electrodes."

Figure 3:
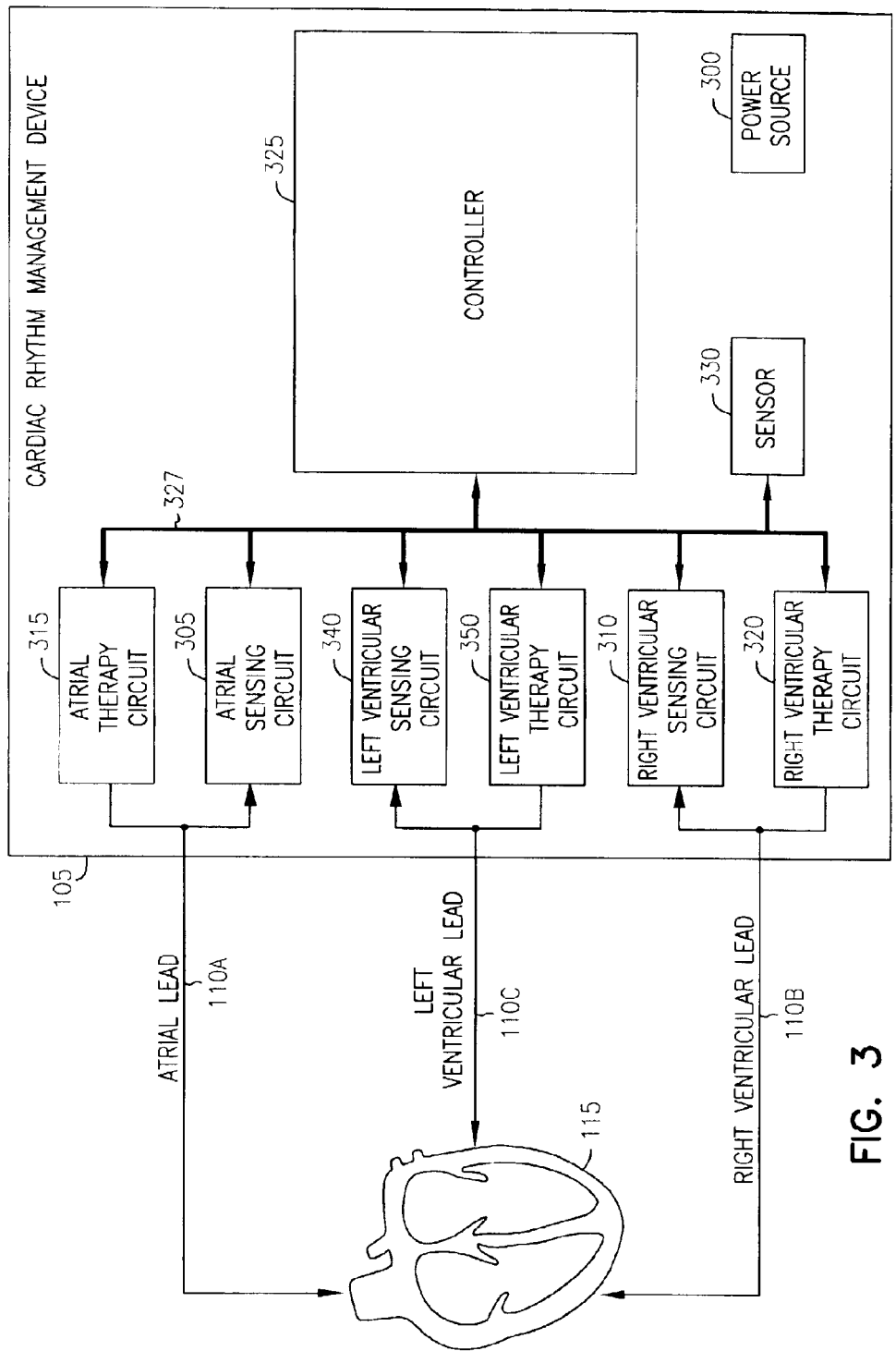
FIG. 3 is a schematic diagram illustrating generally one embodiment of portions of a cardiac rhythm management device coupled to a heart.

FIG. 3 is a schematic diagram illustrating generally, by way of example, but not by way of limitation, one embodiment of portions of device 105, which is coupled to heart 115. Device 105, as shown in FIG. 3, includes a power source 300, an atrial sensing circuit 305, a right ventricular sensing circuit 310, a left ventricular sensing circuit 340, an atrial therapy circuit 315, a right ventricular therapy circuit 320, a left ventricular therapy circuit 350 and a controller 325. The therapy circuits may also be referred to as signal generators for producing pulses applied to the heart. It should be noted that many of the elements of device 105 are optional, depending upon the desired pacing mode. For example, an atrial therapy circuit 315 would not be required for pacing modes such as VVI, VDD or others not utilizing atrial pacing. As a further example, individual sensing circuits 305, 310 or 340 would not be required where their associated leads 110 are utilized only for application of therapy. Other combinations and permutations will be apparent to those skilled in the art.

Atrial sensing circuit 305 is coupled by atrial lead 110A to heart 115 for receiving, sensing, and/or detecting electrical atrial heart signals. Such atrial heart signals include atrial activations (also referred to as atrial depolarizations or P-waves), which correspond to atrial contractions. Such atrial heart signals include normal atrial rhythms, and abnormal atrial rhythms including atrial tachyarrhythmias, such as atrial fibrillation, and other atrial activity. Atrial sensing circuit 305 provides one or more signals to controller 325, via node/bus 327, based on the received atrial heart signals. Such signals provided to controller 325 indicate, among other things, the presence of atrial fibrillation.

Right ventricular sensing circuit 310 is coupled by ventricular lead 110B to heart 115 for receiving, sensing, and/or detecting electrical right ventricular heart signals, such as ventricular activations (also referred to as ventricular depolarizations or R-waves), which correspond to ventricular contractions. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Right ventricular sensing circuit 310 provides one or more signals to controller 325, via node/bus 327, based on the received right ventricular heart signals. Such signals provided to controller 325 indicate, among other things, the presence of ventricular depolarizations, whether regular or irregular in rhythm.

Left ventricular sensing circuit 340 is coupled by ventricular lead 110C to heart 115 for receiving, sensing, and/or detecting electrical left ventricular heart signals, such as ventricular activations. Such ventricular heart signals include normal ventricular rhythms, and abnormal ventricular rhythms, including ventricular tachyarrhythmias, such as ventricular fibrillation, and other ventricular activity, such as irregular ventricular contractions resulting from conducted signals from atrial fibrillation. Left ventricular sensing circuit 340 provides one or more signals to controller 325, via node/bus 327, based on the received left ventricular heart signals. Such signals provided to controller 325 indicate, among other things, the presence of ventricular depolarizations, whether regular or irregular in rhythm.

Atrial therapy circuit 315 provides atrial pacing therapy, as appropriate, to electrodes located at or near the right atrium 200A of heart 115 for obtaining resulting evoked atrial depolarizations. In one embodiment, atrial therapy circuit 315 also provides cardioversion/defibrillation therapy, as appropriate, to electrodes located at or near the right atrium 200A of heart 115, for terminating atrial fibrillation and/or other atrial tachyarrhythmias.

Right ventricular therapy circuit 320 provides ventricular pacing therapy, as appropriate, to electrodes located at or near the right ventricle 205A of heart 115 for obtaining resulting evoked ventricular depolarizations. In one embodiment, right ventricular therapy circuit 320 also provides cardioversion/defibrillation therapy, as appropriate, to electrodes located at or near the right ventricle 205A of heart 115, for terminating ventricular fibrillation and/or other ventricular tachyarrhythmias.

Left ventricular therapy circuit 350 provides ventricular pacing therapy, as appropriate, to electrodes located at or near the left ventricle 205B of heart 115 for obtaining resulting evoked ventricular depolarizations. In one embodiment, left ventricular therapy circuit 350 also provides cardioversion/defibrillation therapy, as appropriate, to electrodes located at or near the left ventricle 205B of heart 115, for terminating ventricular fibrillation and/or other ventricular tachyarrhythmias.

Controller 325 controls the delivery of therapy by ventricular therapy circuits 320/350 and/or other circuits, based on heart activity signals received from atrial sensing circuit 305 and ventricular sensing circuits 310/340. Controller 325 includes various modules, which are implemented either in hardware or as one or more sequences of instructions carried out on a processor or other controller. It is understood that the various modules of controller 325 need not be separately embodied, but may be combined and/or otherwise implemented, such as in software/firmware.

In general terms, sensing circuits 305, 310 and 340 sense electrical signals from heart tissue in contact with the catheter leads 110A–C to which these sensing circuits 305, 310 and 340 are coupled. Sensing circuits 305, 310 and 340 and/or controller 325 process these sensed signals. Based on these sensed signals, controller 325 issues control signals to therapy circuits, such as atrial therapy circuit 315 and ventricular therapy circuits 320 and 350, if necessary, for the delivery of electrical energy (e.g., pacing and/or defibrillation pulses) to the appropriate electrodes of leads 110A–C. Controller 325 may include a microprocessor or other controller for execution of software and/or firmware instructions. The software of controller 325 may be modified (e.g., by remote external programmer 105) to provide different parameters, modes, and/or functions for the implantable device 105 or to adapt or improve performance of device 105.

In a further embodiment, one or more sensors, such as sensor 330, may serve as inputs to controller 325 for adjusting the rate at which pacing or other therapy is delivered to heart 115. One such sensor 330 includes an accelerometer that provides an input to controller 325 indicating increases and decreases in physical activity, for which controller 325 increases and decreases pacing rate, respectively. Another such sensor includes an impedance measurement, obtained from body electrodes, which provides an indication of increases and decreases in the patient's respiration, for example, for which controller 325 increases and decreases pacing rate, respectively. Any other sensor 330 providing an indicated pacing rate can be used.

The multiple ventricular leads each having at least one electrode as shown in FIGS. 2 and 3 permit a certain amount of redundancy in terms of patient therapy, particularly in terms of bradycardia therapy. If one ventricular lead and/or electrode on the lead, for whatever reason, exhibits behavior indicative of failure, the other lead and/or electrode(s) can be used as a redundant system and provide pacing therapy. While coordinating CHF therapy may be compromised or reduced in this example, the device could continue to provide normal bradycardia therapy, or life support.

In devices where lead electrodes are bipolar electrodes, a reversion from bipolar configuration to unipolar configuration upon indication of a failure of the bipolar lead is possible. Such bipolar to unipolar reversion may be a desirable first action in response to indication of failure, with a lead reversion as described herein used as a second action if the bipolar to unipolar reversion does not resolve the failure condition sufficient to maintain the desired pacing therapy.

As used herein, failure generally refers to any condition prohibiting or frustrating use of the lead or electrode in the desired manner during normal operation of the cardiac rhythm management system. This is not limited to physical conditions of the lead or lead/tissue interface, but also includes associated circuitry, power source, software, memory depletion, external factors, e.g., electromagnetic interference (EMI), and unintended effects of stimulation such as abnormal muscle/nerve stimulation. Examples of failures include, but are not limited to, the detection of an over-sense condition, sensed noise, lead impedance outside a predetermined range, detection of capture failure, capture amplitude voltage outside a predetermined range, intrinsic amplitude outside a predetermined range, failure to detect an expected event, an electrical hardware failure, software failure, memory failure, battery depletion and detection of unintended non-cardiac stimulation.

One example of a failure indication includes over-sense conditions. This may be external EMI or noise at a level where the device can no longer reliably sense on that lead. Typically noise is detected by a retriggerable noise window initiated on a sensed event. A subsequent sensed event inside the noise window causes it to retrigger (be extended). A noise condition causes the noise window to be continuously retriggered so that after some time limit (often the pacing escape time), if the noise window is still active, a noise condition is declared (detected) and site reversion could occur. It may further be a sensed condition that is outside of expected values such that the reliability of the sensed condition is questionable. For example, sensed amplitudes far above the sensing detected threshold.

Another example of a failure indication may be based on lead impedance. Leads are often automatically checked for lead impedance, e.g., about once a day. Another example of a failure indication may be based on lead impedance. In one embodiment, the cardiac rhythm management system includes circuitry that is capable of measuring the lead impedance (the impedance seen by the device across a pacing lead or sensing lead). A typical method for determining the lead impedance is to measure the output voltage at two points in time during the delivery of a pace pulse. The pacing voltage in cardiac rhythm management devices is typically stored on a capacitor that partially discharges during the delivery of the pacing pulse. Since the value of this capacitor and the time between the voltage measurements are known, the lead impedance can be readily calculated. Lead impedance measurements that fall outside a previously determined minimum or maximum can indicate lead failure. It is possible to revert from a pacing configuration that uses a proximal electrode and a distal electrode on a single lead (bipolar configuration) to a pacing configuration that utilizes only the distal electrode. Lead failure can also be detected when the lead impedance measurement falls outside a previously determined minimum or maximum. Detection of a lead impedance that is outside a previously determined range can also trigger a reversion to an alternate electrode or lead, within the ventricles if the failed lead is in a ventricle or within the atria if the failed lead is in an atrium, for which the lead impedance is within a previously determined range, thereby mitigating the failure. If the lead impedance gets either too high or too low, the lead or the tissue near the lead can be deemed bad. In such conditions, it is presumed that the therapy is no longer effective or potentially desirable on that site, so reversion to another site may be desirable.

A further example of a failure condition may be based on automatic detection of capture failure. Capture is the condition of activating contraction of the cardiac muscle by paced stimulation. One such method of detecting capture failure has a dedicated unipolar evoked response channel with low capacitance that can detect the evoked response of the cardiac muscle activation following the pacing artifact. When the evoked response following the pacing pulse falls below an evoked response threshold, loss of capture is declared. When capture failure is detected, pacing is switched to an alternative pacing site.

A related example of a failure condition may be based on the pacing amplitude that is automatically adjusted by an autocapture system. If the pacing amplitude required to capture becomes too high, the device may excessively deplete the battery or the device may be unable to maintain reliable capture at that site. Thus a failure condition may be detected when the capture amplitude exceeds a threshold and site reversion could occur.

Yet another example of a failure indication may be based on intrinsic sensed potential amplitude. Device sensing circuits can measure the voltage of the electrical signal generated by the heart near a sensing lead electrode. If the maximum or average amplitude of this intrinsic signal falls below a threshold, sensing at that site may be compromised and declared in failure so that reversion to an alternate sensing site could occur.

Circuit failures would also constitute a failure indication. Examples may include failure of an individual sensing circuit or a therapy circuit, or loss of a pacing parameter in the controller. While global circuit failures may moot the recovery mechanisms described herein, e.g., lead reversion will be ineffective in the case of a power source failure, local circuit failures may be amenable to such recovery mechanisms.

Another example of failure indication may be based on battery depletion. In one embodiment, the cardiac rhythm management device monitors the status of the battery to, among other reasons, alert the clinician when device replacement is required. Methods of monitoring the battery status can include, but are not limited to, battery voltage measurement, the time required to replenish the therapy power supply after delivery of therapy, or a combination of the two. In an additional embodiment, the detection of a previously determined depletion level of the battery is used to trigger a change in the pacing mode, defibrillation therapy mode and diagnostic capabilities of the device in an attempt to lengthen the remaining life of the device. Examples include, changing the pacing therapy from a mode that paces and/or senses both an atrium and a ventricle to one that paces and/or senses only a ventricle. Use of the detection of a previously determined depletion level of the battery is also used to trigger a reversion to an alternate and/or fewer pacing/sensing site(s) within the atria or within the ventricles in such a way as to reduce the current drain.

Another example of failure indication may be based on memory corruption. The integrity of the device memory is monitored. In one example, a method of monitoring the memory includes the use of Cycle Redundancy Checking (CRC) and hamming encryption/decryption. Via these or other methods a memory fault can be detected. The use of memory corruption detection is used to change the therapy of a cardiac rhythm management device. The pacing mode can also be modified when memory corruption occurs. In one embodiment, pacing mode modification pertains to the addition or deletion of a single atrial or ventricular pacing/sensing site. Alternatively, use of the detection of a memory fault triggers a reversion to more, fewer, and/or an alternate pacing/sensing site(s) within the atria or within the ventricles.

A still further example of a failure indication can be based on multiple site cross-checking. Excitatory heart tissue naturally propagates electrical activation from one region to another (conduction) as part of its function to generate coordinated contraction within a heart chamber and between left and right chambers of the heart. With a multisite design, multiple leads and/or electrodes are placed within a single heart chamber and/or in both left and right chambers. Due to natural electrical propagation in heart tissue, activation sensed or initiated by pacing at one site will be followed after a predictable conduction delay by sensed activation at another site. Thus, verification of pace capture or sensed activation at one site can be cross-checked by sensing conducted events at another site. For example, if paced capture occurs at a primary site, activation will be sensed at a second site after a conduction delay dependent largely on the distance separating the two sites. If activation is not sensed at the second site within an expected conduction delay window, a failed capture condition is detected at the pacing site and site reversion could occur for a backup pace or for pacing on subsequent cardiac cycles. As another example, if activation is detected by sensing at a primary site, a paired activation will be detected at a second sensing site either just earlier or just later than at the primary site due to conduction. If activation is not detected at the second sensing site within the expected conduction delay window before and/or after detection at the primary site, the detection at the primary site may be due to a failure condition (e.g., sensed noise, over-sensing) and sensing site reversion can occur.

Another example of cross-checking is based on a fundamental behavior of implantable pacemakers to inhibit (prevent) or delay a scheduled pacing stimulation when a natural heart activation is detected by the sensing function prior to the scheduled pace. This pacing inhibition has two purposes: 1) it prevents unnecessary pacing when the natural heart rate is faster than the indicated pacing rate; 2) it prevents pacing during a period of time following heart tissue activation during which a pacing stimulation might induce a tachycardia (this is referred to as the vulnerable period). As a first example, when a sensed event is detected at a primary pacing/sensing site, pacing is immediately inhibited in the current cardiac cycle and rescheduled for the next cycle at the indicated rate. As a second example, when a sensed event is detected at a primary pacing/sensing site, an inhibitory period with duration longer than the vulnerable period is initiated during which pacing will be inhibited. When a pace is scheduled to occur during the inhibitory period, it will be inhibited and either rescheduled for some time after the end of the inhibitory period or rescheduled for the next cardiac cycle at the indicated rate. In these examples, if there is a sensing failure at the primary sensing site due to a noise or over-sensing condition, a false sense may be detected that will inappropriately inhibit pacing for that cycle or initiate an inhibitory period during which pacing will be inappropriately inhibited. In this situation, a second sensing site is used to cross-check the correctness of the sensing at the primary site. Following a sensed detection at the primary site, if a paired sense is not detected at the second site after an expected conduction delay, the sensing at the first site is determined to be failed, causing reversionary correction of pacing inhibition. Examples of this correction include, but are not limited to, pacing immediately at a secondary site or at the primary site, ignoring the inhibitory effect of the sensed event on the pacing schedule and resuming the previous pacing schedule, or canceling any triggered inhibitory period.

As an example, in univentricular LV pacing, a pace may be inhibited in a cardiac cycle due to a sensed LV activation. In response to the inhibition, a lead in the RV could be used to verify the sensed LV activation. Failure to sense the LV activation by the lead in the RV could be used as an indication of failure of the lead in the LV. Despite the inhibition of the pace to the LV, it may be desirable to revert therapy to the lead in the RV for pacing in that chamber of the heart.

Another example of a failure indication can be based on detecting unintended stimulation of non-cardiac tissue, such as phrenic nerve stimulation (causing "hiccups") or thoracic muscle stimulation (e.g., "pocket twitch"). Such detection can be based on device lead sensing of voltage potentials associated with the paced stimulation that are larger than or have different morphology than the expected evoked response from cardiac tissue or are potentials that do not follow expected cardiac conduction delays and patterns. A further means of detecting such unintended stimulation would be to use additional device sensors capable of detecting thoracic muscle movement, such as a pacemaker accelerometer sensor or thoracic impedance sensor, either of which measures patient movement and breathing. When unintended stimulation is detected due to pacing at one site, reversion to an alternate pacing site and/or an alternate pacing vector can occur to try to avoid the non-cardiac stimulation.

In general, any abnormality may be used as a failure indication if it is indicative that sensing, pacing or defibrillation on an individual lead is other than desired. While the following will be described in terms of sensing and pacing, it should be recognized that defibrillation pulses can be applied in like manner to pacing pulses. Accordingly, the following does not preclude defibrillation therapy.

Figure 4:
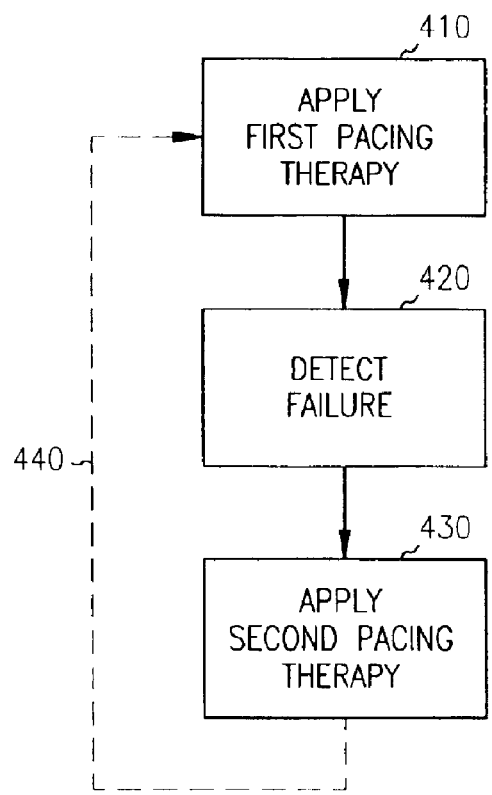
FIG. 4 is a flowchart showing one embodiment of providing pacing therapy.

FIG. 4 is a flowchart showing one embodiment of providing pacing therapy. In FIG. 4, a first pacing therapy is applied in action box 410. The first pacing therapy may be applied using one or more leads each having at least one electrode, and involving one or more chambers of the heart. Individual leads may be used for sensing only, pacing only, both sensing and pacing, or neither sensing nor pacing. Furthermore, individual leads may have two or more electrodes acting independently. Leads or electrodes not used for sensing or pacing will be referred to as redundant.

Figure 5:
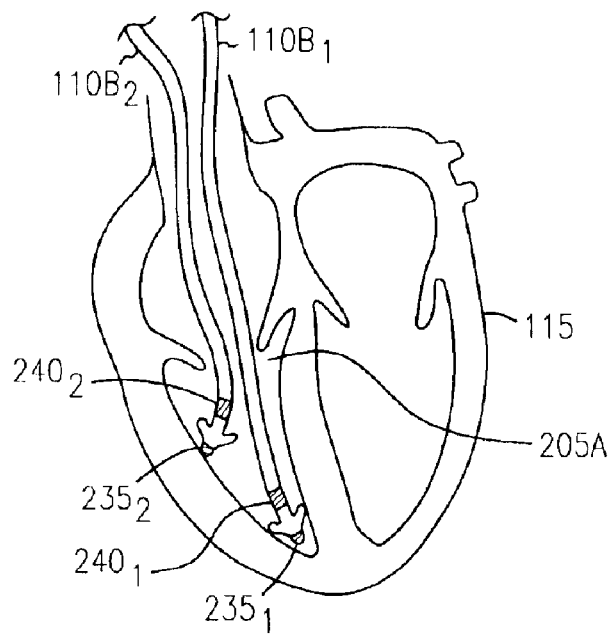
FIG. 5 is a schematic drawing illustrating one embodiment of a portion of a cardiac rhythm management device coupled by leads to a heart.

FIG. 5 is a schematic illustrating but one example of a system having the capability for lead redundancy as described above. FIG. 5 generally depicts a portion of the device of FIG. 2, although some leads are omitted for clarity. FIG. 5 differs from FIG. 2 in that right ventricle lead 110B is replaced by a first right ventricle lead 110B$_1$ and a second right ventricle lead 110B$_2$. One or both of the right ventricle leads 110B may be actively sensing or pacing during the first pacing therapy. While there are only two right ventricle leads 110B depicted in FIG. 5, additional right ventricle leads may be utilized. Although there may be a practical limit as to how many leads may be associated with an individual chamber of the heart, the methods described herein may be applied to any number of available leads. Furthermore, use of the right ventricle as an example for FIG. 5 is not limiting and redundant or multiple leads may be utilized in any chamber of the heart. In addition, electrodes 235$_1$/235$_2$ may act as redundant electrodes to electrodes 240$_1$/240$_2$, respectively.

Referring again to FIG. 4, lead failure is detected in action box 420 using one or more of the failure indications as described above. Lead failure may involve one or more leads. However, to provide effective reversion, at least one lead or electrode available for pacing therapy should not indicate failure. Subsequent to detection of a failure, a second pacing therapy is applied in action box 430. The second pacing therapy may be applied using one or more of the leads used for the first pacing therapy.

As one example, a device as in FIG. 2 may be used for coordinating CHF therapy using a biventricular DDD pacing mode as the first pacing therapy. Such a pacing therapy would use leads 110A, 110B and 110C. Detection of a failure of the left ventricle lead 110C could be used to initiate application of the second pacing therapy. One example of a second pacing therapy could be univentricular DDD pacing mode using leads 110A and 110B. If a failure were simultaneously or subsequently detected on the atrial lead 110A, an acceptable second pacing therapy may be VVI pacing mode using only right ventricle lead 110B. In general, any pacing therapy can be chosen provided that the detected failure does not interfere with the pacing therapy. Note that a detected failure affecting sensing on a lead may not interfere with pacing on that lead, and vice versa. Furthermore, a detected failure affecting one electrode on a lead having multiple electrodes may not interfere with sensing or pacing on other electrodes on the lead.

As further example, a device as in FIG. 5 may be used for VVI pacing mode as the first pacing therapy using at least one right ventricle lead 110B. Detection of a failure of one right ventricle lead 110B could be used to initiate application of the second pacing therapy. One example of a second pacing therapy could be VVI pacing mode using one or more right ventricle leads 110B not indicating failure. In general, any pacing therapy can be chosen provided that the detected failure does not interfere with the pacing therapy. Note that a detected failure affecting sensing on a lead may not interfere with pacing on that lead, and vice versa. Note further that the second pacing therapy may utilize the same pacing mode as the first pacing therapy, albeit using a different set of one or more leads.

Dashed line 440 in FIG. 4 indicates that it may be desirable to apply the second pacing therapy only temporarily. For example, upon detection of a failure in action box 420, the second pacing therapy may be applied in action box 430 only for one cardiac cycle, resuming the first pacing therapy in action box 410 on the next cardiac cycle. Alternatively, the second pacing therapy may be applied until the failure indication is resolved, e.g., a noise source is removed, normal sensing resumes, impedance measurements return to expected values, etc. Upon resolution of the failure indication, the first pacing therapy is resumed in action box 410. The second pacing therapy may alternatively be latched such that physician intervention is required to resume the first pacing therapy.

Figure 6:
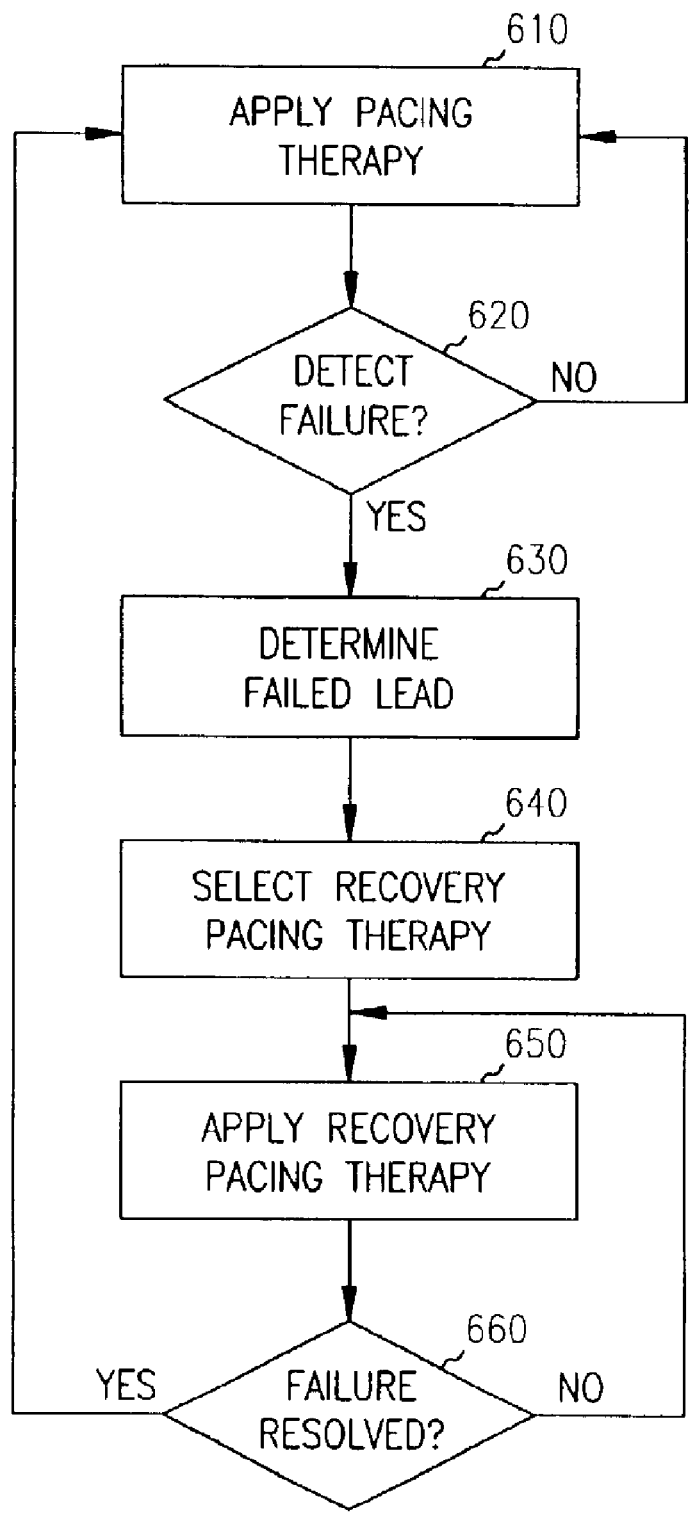
FIG. 6 is a flowchart showing one embodiment of providing pacing therapy.

FIG. 6 is a flowchart of another embodiment of providing pacing therapy through a cardiac rhythm management device. The device applies a pacing therapy in action box 610 as a first pacing therapy. The device determines if a failure indication has been detected in decision box 620. If no failure is indicated, the device continues to apply the first pacing therapy and monitor for detection of failure. If lead failure is indicated, control is passed to action box 630.

The device determines which lead is indicating failure in action box 630. Based on the remaining leads having an acceptable status for sensing and/or pacing, a recovery pacing therapy is selected in action box 640 as a second pacing therapy. Selection of the recovery pacing therapy is a design choice generally dependent upon the leads available for sensing and pacing as well as the patient's needs. Accordingly, available choices may be partially directed by a physician, preferably during programming of the device. Selection may be based on a lookup table, providing a single pacing mode for each combination of available leads. Selection may also take into consideration metabolic demand, e.g., providing a first selection for a first demand level and a second selection for a second demand level.

Upon application of a recovery pacing therapy in action box 650, the device can monitor for failure resolution, i.e., removal or disappearance of the failure condition, in decision box 660. If the failure indication remains, the device can continue to apply the recovery pacing therapy and to monitor for failure resolution. If the failure is resolved, the device can pass control back to action box 610 for resumption of the first pacing therapy.

While the foregoing description was in the context of a first pacing therapy and second pacing therapy, devices having multiple leads may be amenable to multiple tiers of failure recovery. As an example, a second pacing therapy may be applied in response to a first lead failure as described above. However, the device may be capable of sustaining more than one lead failure depending upon the failure type, i.e., sensing, pacing or both, and the number of available leads. Upon detection of a subsequent lead failure prior to resolution of the first lead failure, the device may revert to a third pacing therapy from the second pacing therapy in the same manner as described for the reversion to the second pacing therapy from the first pacing therapy.

Furthermore, certain reversionary behavior may be contraindicated. For example, certain reversion may not be desirable if triggered pacing is enabled, e.g., reversion from a left trigger situation to a right trigger situation may result in undesirable timing. However, reversion to some therapy, particularly life sustaining therapy, is likely more desirable than continuing the first pacing therapy despite the failure indication or simply discontinuing pacing therapy altogether.

Figure 7:
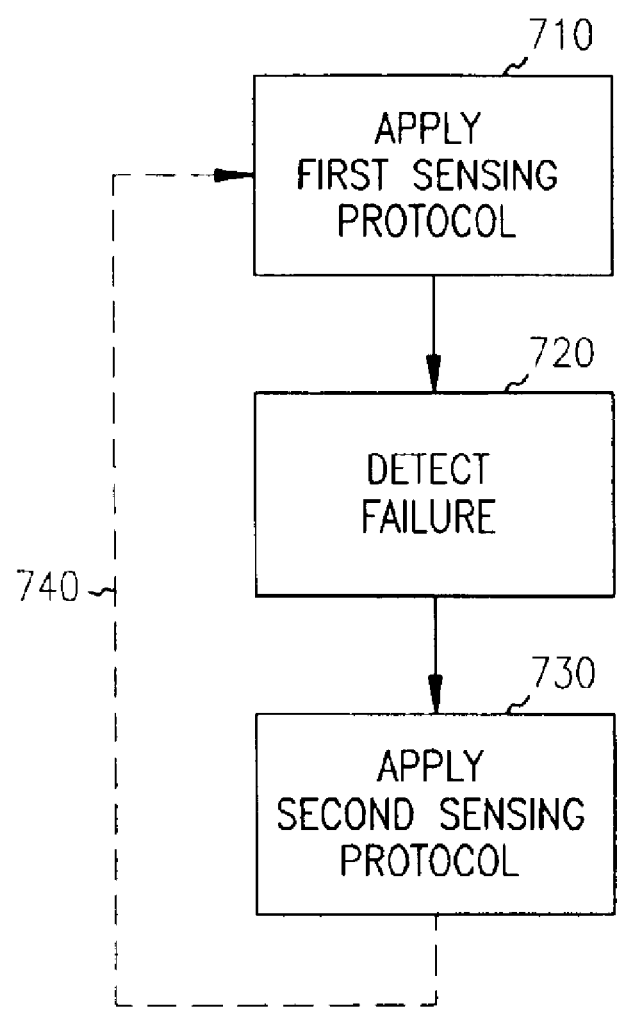
FIG. 7 is a flowchart showing one embodiment of providing sensing protocols.

In an additional embodiment, a second sensing protocol is used either alone or in combination with the second pacing therapy after detecting a lead failure. FIG. 7 is a flowchart showing one embodiment of site reversion for cardiac sensing, where the site reversion for cardiac sensing occurs either in combination with the site reversion for pacing or where the lead failure only causes a site reversion for cardiac sensing.

In FIG. 7, a first sensing protocol is applied in action box 710. The first sensing protocol may be accomplished using one or more leads having one or more electrodes and involving one or more chambers of the heart. Individual leads may be used for sensing only, pacing only, both sensing and pacing, or neither sensing nor pacing. Furthermore, individual leads may have two or more electrodes acting independently. Leads or electrodes not used for sensing or pacing are referred to as redundant.

At 720, a sensing, lead and/or electrode failure is detected using one or more of the failure indications as described above. Lead failure may involve one or more leads. However, to provide effective reversion, at least one lead or electrode available for sensing and/or pacing therapy should not indicate failure. Subsequent to detection of a failure, a second sensing protocol is invoked in action box 730. The second sensing protocol may be applied using one or more of the leads and/or electrodes used for the first sensing protocol. Dashed line 740 in FIG. 7 indicates that it may be desirable to use the second sensing protocol only temporarily. For example, upon detection of a failure in action box 720, the second sensing protocol may be used in action box 730 only for one cardiac cycle, resuming the first sensing protocol in action box 710 on the next cardiac cycle. Alternatively, the second sensing protocol may be used until the failure indication is resolved, e.g., a noise source is removed, normal sensing resumes, impedance measurements return to expected values, etc. Upon resolution of the failure indication, the first sensing protocol is resumed in action box 710. The second sensing protocol may alternatively be latched such that physician intervention is required to resume the first sensing protocol.

Figure 8:
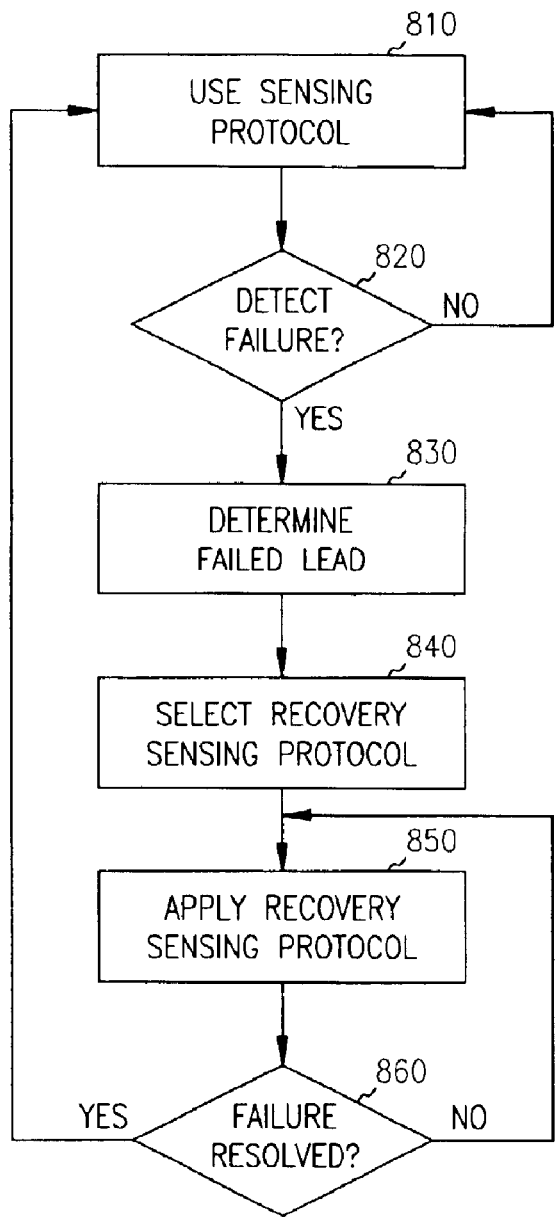
FIG. 8 is a flowchart showing one embodiment of providing sensing protocols.

FIG. 8 is a flowchart an embodiment of sensing cardiac signals through a cardiac rhythm management device. The device senses one or more cardiac signals in action box 810 in a first sensing protocol. The device determines if a failure indication has been detected in decision box 820. If no failure is indicated, the device continues to sense cardiac signals using the first sensing protocol and monitor for detection of failure. If lead failure is indicated, control is passed to action box 830.

The device determines which lead is indicating failure in action box 830. Based on the remaining leads having an acceptable status for sensing and/or pacing, a recovery sensing protocol is selected in action box 840 as a second sensing protocol. Selection of the recovery sensing protocol is a design choice generally dependent upon the leads available for sensing and pacing as well as the patient's needs. Accordingly, available choices may be partially directed by a physician, preferably during programming of the device. Selection may be based on a lookup table, providing a single pacing mode and/or sensing mode for each combination of available leads. Selection may also take into consideration metabolic demand, e.g., providing a first selection for a first demand level and a second selection for a second demand level.

Upon application of a recovery sensing protocol in action box 850, the device can monitor for failure resolution, i.e., removal or disappearance of the failure condition, in decision box 860. If the failure indication remains, the device can continue to apply the recovery sensing protocol and to monitor for failure resolution. If the failure is resolved, the device can pass control back to action box 810 for resumption of the first sensing protocol.

While the foregoing description was in the context of a first sensing protocol and second sensing protocol, devices having multiple leads may be amenable to multiple tiers of failure recovery. As an example, a second sensing protocol may be applied in response to a first lead failure as described above. However, the device may be capable of sustaining more than one lead failure depending upon the failure type, i.e., sensing, pacing or both, and the number of available leads. Upon detection of a subsequent lead failure prior to resolution of the first lead failure, the device may revert to a third sensing protocol from the second sensing protocol in the same manner as described for the reversion to the second sensing protocol from the first sensing protocol.

Figure 9:
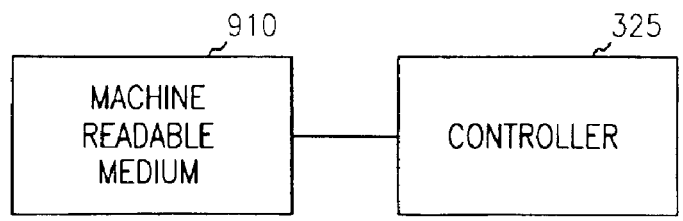
FIG. 9 is a schematic drawing illustrating generally one embodiment of portions of a cardiac rhythm management system having a machine readable medium.

The methods described herein may generally be carried out by a controller or processor as a sequence of instructions. The instructions may be stored on a machine readable medium 910, such as ROM or flash memory, coupled to the controller 325 as shown in FIG. 9. Machine readable medium 910 may be programmed by the programmer 125 and telemetry unit 130, as shown in FIG. 1, through controller 325. Alternatively, machine readable medium 910 may be preprogrammed such that physician intervention is prevented.

CONCLUSION

Although specific embodiments have been illustrated and described herein, it will be appreciated by those of ordinary skill in the art that any arrangement which is calculated to achieve the same purpose may be substituted for the specific embodiments shown. Many adaptations of the invention will be apparent to those of ordinary skill in the art. For example, use of markers or other display mechanisms to indicate reversion or the number of reversions may be used to assist the physician during interrogation of the cardiac rhythm management device. Different lead types, numbers of leads, and utilized heart chambers can be varied from the examples depicted herein. As examples, rather than a biventricular three-chamber therapy as described with reference to FIG. 2, a biatrial three-chamber therapy or biatrial/biventricular four-chamber therapy could be accommodated by the embodiments described herein. Accordingly, this application is intended to cover any adaptations or variations of the invention. It is manifestly intended that this invention be limited only by the following claims and equivalents thereof.

What is claimed is:

1. A method comprising:
   delivering a first therapy through a first electrode in a first chamber;
   detecting an anomaly associated with the first electrode;
   discontinuing the first therapy; and
   delivering a second therapy to a second chamber through a second electrode.

2. The method of claim 1, wherein discontinuing the first therapy includes discontinuing the first therapy during the anomaly associated with the first electrode, and where delivering the second therapy includes delivering the second therapy to the second electrode during the anomaly associated with the first electrode.

3. The method of claim 1, including operating the first electrode in at least one mode selected from the group consisting of bipolar and unipolar, and wherein delivering the second therapy to the second electrode only occurs when the first electrode is operating in the unipolar mode.

4. The method of claim 1, wherein detecting the anomaly associated with the first electrode includes but is not limited to detecting a condition selected from the group consisting of an over-sense condition, sensed noise, lead impedance outside a predetermined range, capture amplitude voltage outside a predetermined range, intrinsic amplitude outside a predetermined range, detection of unintended non-cardiac stimulation, and failure to detect an expected event.

5. The method of claim 1, wherein detecting the anomaly includes detecting a failure associated with the first electrode.

6. The method of claim 1, wherein the first therapy is a first pacing therapy and the second therapy is a second pacing therapy.

7. The method of claim 1, including implanting the first electrode and the second electrode through the coronary sinus vein.

8. The method of claim 7, including positioning the first electrode and the second electrode adjacent the left ventricle.

9. A method comprising:
   delivering a first therapy through a first lead having at least one electrode in a first chamber;
   detecting an anomaly associated with the first lead;
   discontinuing the first therapy; and
   delivering a second therapy to a second lead in a second chamber after detecting the failure type anomaly.

10. The method of claim 9, wherein discontinuing the first therapy includes discontinuing the first therapy during the anomaly associated with the first lead.

11. The method of claim 9, including operating the at least one electrode of the first lead in at least one mode selected from the group consisting of bipolar and unipolar, and wherein delivering the second therapy only occurs when the at least one electrode of the first lead is operating in the unipolar mode.

12. The method of claim 9, wherein detecting the anomaly associated with the first lead includes but is not limited to detecting a condition selected from the group consisting of an over sense condition, sensed noise, lead impedance outside a predetermined range, capture amplitude voltage outside a predetermined range, intrinsic amplitude outside a predetermined range, detection of unintended non-cardiac stimulation, and failure to detect an expected event.

13. The method of claim 9, wherein detecting the anomaly associated with the first lead includes but is not limited to detecting a condition selected from the group consisting of an electrical hardware failure, software failure, memory failure and battery depletion.

14. The method as recited in claim 9, wherein discontinuing the first therapy and delivering the second therapy include reverting from a bipolar therapy to a unipolar therapy.

15. The method as recited in claim 9, further comprising positioning the first lead and the at least one electrode in the right ventricle, and positioning the second lead adjacent the left ventricle.

16. The method as recited in claim 9, further comprising positioning the first lead and the at least one electrode in the right atrium, and positioning the second lead adjacent the left atrium.

17. The method as recited in claim 9, further comprising positioning the first lead and the at least one electrode adjacent the left ventricle, and positioning the second lead in the right ventricle.

18. The method as recited in claim 9, further comprising positioning the first lead and the at least one electrode adjacent the left atrium, and positioning the second lead in the right atrium.

19. The method as recited in claim 9, further comprising coupling the first lead to a first atrium and coupling the second lead to a first ventricle.

20. A cardiac rhythm management system, comprising:
   a signal generator;
   a first electrode adapted for connection to the signal generator;
   a second electrode adapted for connection to the signal generator;
   means for indicating presence of a failure with the first electrode; and
   means for reverting from delivering a first therapy to the first electrode in a first chamber, to delivering a second therapy to the second electrode in a second chamber in the presence of a failure associated with the first electrode.

21. The cardiac rhythm management system of claim 20, wherein delivering the first therapy to the first electrode includes delivering the first therapy to both the first and second electrodes.

22. The cardiac rhythm management system of claim 15, wherein delivering the first therapy to the first and second electrodes includes delivering a first pulse to the first electrode and a second pulse to the second electrode.

23. The cardiac rhythm management system of claim 20, including a lead adapted for connection to the signal generator, the lead comprising a main lead body adapted to carry signals to and from the heart, where the first electrode and the second electrode are carried by the main lead body.

24. The cardiac rhythm management system of claim 23, where the lead is adapted to be implanted through the coronary sinus vein.

25. A cardiac rhythm management system, comprising:
a signal generator;
a first electrode adapted for connection to the signal generator;
a second electrode adapted for connection to the signal generator; and
a processor coupled to the signal generator, wherein the processor is adapted to cause the signal generator to deliver a first therapy to a first chamber through the first electrode, and to deliver a second therapy to a second chamber through the second electrode in the presence of an anomaly associated with the first electrode.

26. The cardiac rhythm management system of claim 25, wherein delivering the first therapy to the first electrode includes delivering the first therapy through both the first and second electrodes.

27. The cardiac rhythm management system of claim 26, wherein delivering the first therapy through the first and second electrodes includes delivering a first pulse to the first electrode and a second pulse to the second electrode.

28. The cardiac rhythm management system of claim 27, wherein the pulses applied to the second electrode in the second therapy are substantially similar to the pulses applied to the first electrode in the first therapy.

29. The cardiac rhythm management system of claim 25, wherein the first electrode is adapted to operate in at least one mode selected from the group consisting of bipolar and unipolar, and wherein the processor is further adapted to cause the signal generator to deliver the second therapy only when the first electrode is operating in the unipolar mode.

30. The cardiac rhythm management system of claim 25, wherein the presence of the anomaly is indicated by detection of a condition selected from the group consisting of an over sense condition, sensed noise, lead impedance outside a predetermined range, capture amplitude voltage outside a predetermined range, intrinsic amplitude outside a predetermined range, detection of unintended non-cardiac stimulation, and failure to detect an expected event.

31. The cardiac rhythm management system of claim 25, wherein the presence of the anomaly is indicated by detection of a condition selected from the group consisting of an electrical hardware failure, software failure, memory failure and battery depletion.

32. The cardiac rhythm management system of claim 25, including a lead adapted for connection to the signal generator, the lead comprising a main lead body adapted to carry signals to and from the heart, where the first electrode and the second electrode are carried by the main lead body.

33. The cardiac rhythm management system of claim 25, further comprising:
a first lead having at least one of the first or second electrodes;
a second lead having the other of the first or second electrodes.

* * * * *